United States Patent
Sikora et al.

(10) Patent No.: US 7,491,212 B2
(45) Date of Patent: Feb. 17, 2009

(54) TRANSMITTING AN ACTUATING FORCE ALONG A CURVED INSTRUMENT

(75) Inventors: George Sikora, Bridgewater, MA (US); Raymond A. Bojarski, Attleboro, MA (US); Aaron Hecker, West Roxbury, MA (US)

(73) Assignee: Smith & Nephew, Inc., Memphis, TX (US)

( * ) Notice: Subject to any disclaimer, the term of this patent is extended or adjusted under 35 U.S.C. 154(b) by 646 days.

(21) Appl. No.: 10/370,276

(22) Filed: Feb. 19, 2003

(65) Prior Publication Data
US 2004/0162569 A1    Aug. 19, 2004

(51) Int. Cl.
A61B 17/04    (2006.01)
(52) U.S. Cl. .................................... 606/148
(58) Field of Classification Search .............. 606/138, 606/139, 144, 145, 148, 83, 159, 170, 184, 606/185; 289/2, 12, 17; 600/566, 567, 585
See application file for complete search history.

(56) References Cited

U.S. PATENT DOCUMENTS

| | | | |
|---|---|---|---|
| 919,138 A | 4/1909 | Drake et al. | |
| 2,416,260 A | 2/1947 | Karle | |
| 4,224,947 A | 9/1980 | Fukuda | |
| 4,384,406 A | 5/1983 | Tischlinger | |
| 4,471,781 A | 9/1984 | Di Giovanni et al. | |
| 4,509,516 A | 4/1985 | Richmond | |
| 4,586,502 A | 5/1986 | Bedi et al. | |
| 4,602,635 A | 7/1986 | Mulhollan et al. | |
| 4,621,639 A | 11/1986 | Transue et al. | |
| 4,624,254 A | 11/1986 | McGarry et al. | |
| 4,646,738 A | 3/1987 | Trott | |
| 4,724,840 A | 2/1988 | McVay et al. | |
| 4,787,377 A | 11/1988 | Laboureau | |
| 4,898,156 A | 2/1990 | Gatturna et al. | |
| 4,946,468 A | 8/1990 | Li | |
| 4,968,315 A | 11/1990 | Gatturna | |
| 5,002,550 A | 3/1991 | Li | |
| 5,037,433 A | 8/1991 | Wilk et al. | |
| 5,058,661 A | 10/1991 | Oshiyama | |
| 5,078,723 A * | 1/1992 | Dance et al. ................. 606/159 |
| 5,100,418 A | 3/1992 | Yoon et al. | |
| 5,100,421 A | 3/1992 | Christoudias | |

(Continued)

FOREIGN PATENT DOCUMENTS

DE    3831398 A1    3/1990

(Continued)

OTHER PUBLICATIONS

International Search Report, Form PCT/ISA/210, 8 pages.

*Primary Examiner*—Julian W Woo
(74) *Attorney, Agent, or Firm*—Fish & Richardson P.C.

(57) ABSTRACT

In one aspect there is a curved medical instrument comprising an outer member and an inner member. The inner member has a curved portion at a distal region of the inner member. The outer member is concentrically and movably coupled to the inner member and has a flexible transmission mechanism at a distal region of the outer member. The flexible transmission mechanism transmits a linear and/or rotational actuating force along the curved portion of the instrument. The inner member can include an opening configured to receive a target for cutting, such as a flexible fixating member and/or biological tissue.

58 Claims, 5 Drawing Sheets

U.S. PATENT DOCUMENTS

| | | | |
|---|---|---|---|
| 5,129,912 A | 7/1992 | Noda et al. | |
| 5,133,723 A | 7/1992 | Li et al. | |
| 5,163,946 A | 11/1992 | Li | |
| 5,176,691 A | 1/1993 | Pierce | |
| 5,192,287 A | 3/1993 | Fournier et al. | |
| 5,224,955 A | 7/1993 | West | |
| 5,250,054 A | 10/1993 | Li | |
| 5,275,609 A | 1/1994 | Pingleton et al. | |
| 5,287,858 A * | 2/1994 | Hammerslag et al. | 600/585 |
| 5,327,896 A | 7/1994 | Schmieding | |
| 5,376,096 A | 12/1994 | Foster | |
| 5,403,330 A | 4/1995 | Tuason | |
| 5,439,474 A | 8/1995 | Li | |
| 5,443,472 A | 8/1995 | Li | |
| 5,501,692 A | 3/1996 | Riza | |
| 5,527,325 A * | 6/1996 | Conley et al. | 606/159 |
| 5,549,618 A | 8/1996 | Fleenor et al. | |
| 5,562,684 A | 10/1996 | Kammerer | |
| 5,565,122 A | 10/1996 | Zinnbauer et al. | |
| 5,569,269 A | 10/1996 | Hart et al. | |
| 5,632,755 A * | 5/1997 | Nordgren et al. | 606/159 |
| 5,639,506 A | 6/1997 | Smyth | |
| 5,643,296 A * | 7/1997 | Hundertmark et al. | 606/159 |
| 5,653,716 A | 8/1997 | Malo et al. | |
| 5,662,663 A | 9/1997 | Shallman | |
| 5,695,506 A * | 12/1997 | Pike et al. | 606/159 |
| 5,776,114 A * | 7/1998 | Frantzen et al. | 606/170 |
| 5,782,862 A | 7/1998 | Bonutti | |
| 5,797,928 A | 8/1998 | Kogasaka | |
| 5,855,311 A | 1/1999 | Hamblin et al. | |
| 5,864,254 A | 1/1999 | Tashiro | |
| 5,885,293 A | 3/1999 | McDevitt | |
| 5,897,564 A | 4/1999 | Schulze et al. | |
| 5,897,574 A | 4/1999 | Bonutti | |
| 5,904,692 A | 5/1999 | Steckel et al. | |
| 5,908,426 A | 6/1999 | Pierce | |
| 5,928,252 A | 7/1999 | Steadman et al. | |
| 5,941,439 A | 8/1999 | Kammerer et al. | |
| 5,951,575 A | 9/1999 | Bolduc et al. | |
| 6,019,772 A * | 2/2000 | Shefaram et al. | 606/159 |
| 6,036,707 A * | 3/2000 | Spaulding | 606/159 |
| 6,041,485 A | 3/2000 | Pedlick et al. | |
| 6,074,403 A | 6/2000 | Nord | |
| 6,083,177 A | 7/2000 | Kobren et al. | |
| 6,161,543 A | 12/2000 | Cox et al. | |
| 6,235,042 B1 * | 5/2001 | Katzman | 606/159 |
| 6,451,030 B2 | 9/2002 | Li et al. | |
| 6,884,249 B2 * | 4/2005 | May et al. | 606/148 |
| 2002/0128684 A1 | 9/2002 | Foerster | |

FOREIGN PATENT DOCUMENTS

| | | |
|---|---|---|
| EP | 0 717 957 A1 | 6/1996 |
| EP | 0 769 272 A1 | 4/1997 |
| WO | 92/12674 | 8/1992 |
| WO | 96/39946 | 12/1996 |

* cited by examiner

TRANSMITTING AN ACTUATING FORCE ALONG A CURVED INSTRUMENT

TECHNICAL FIELD

This invention relates to medical devices, and more particularly to transmitting an actuating force along a curved instrument.

BACKGROUND

To assist a surgeon when performing a meniscal repair, there is a knot pusher and suture cutter with a straight distal end. The straight suture cutter includes two components at its distal end, one inside the other. The inner component has a hollow tip at the distal end so a surgeon can pass a suture through the tip and out a port on the side of the inner component. The tip of the inner component is designed to push a knot and or receive an attachment to push a knot. The outer component slides over the straight inner component and cuts any suture protruding from the port of the inner component.

SUMMARY

The present application teaches a medical instrument with a curved distal end and a flexible transmission mechanism to transmit an actuating force along that curved distal end. The flexible transmission mechanism is able to negotiate or manage the connection of rigid components over a curved axis. The mechanism permits smooth translation between the rigid elements and an actuating mechanism, between which the flexible transmission mechanism is disposed.

For example, the mechanism allows concentric actuating tube(s) to follow along a rigid, yet curved axis. In one example, the actuating translation is achieved by the placement of strategic relief geometry along the body of a mating component to generate the flexible transmission mechanism. This strategic geometry creates the relief and clearance necessary for the concentrically mating member to transfer linear and/or rotary motion along the curved portion in a smooth translation without binding. The distal working end of the device is curved so that it may provide accessibility to the desired areas that may be inaccessible by traditional non-invasive means. The curved portion negotiates the working trajectory, such as in the application of maneuvering and or accommodating anatomical structures.

In one aspect, there is a medical instrument including an inner member and an outer member. The inner member has a curved portion at its distal region. The outer member is concentrically and movably coupled to the inner member. The outer member includes a flexible transmission mechanism at its distal region. The medical instrument can have one or more of the following features. The flexible transmission mechanism of the outer member can have less material than another portion of the outer member that is less flexible than the flexible transmission mechanism. The outer member can include a wall defining a passage through which the inner member passes. In this example, the wall of the flexible transmission mechanism does not fully enclose the passage of the outer member. In one example, the wall of the flexible transmission mechanism of the outer member can be disposed on a concave side of the curved portion of the inner member. In another example, the wall within the flexible transmission mechanism of the outer member can enclose approximately a range of 30% to 40% of the circumference of the passage.

The outer member can include a first less-flexible portion and a second less-flexible portion. The first less-flexible portion is disposed distal to the flexible transmission mechanism. The second less-flexible portion is disposed proximal to the flexible transmission mechanism. The flexible transmission mechanism is configured to conform to the curved portion while transferring motional forces from the second less-flexible portion to the first less-flexible portion. The motional forces can include linear and/or rotational forces. The outer member can include a first portion and a second portion. The first portion includes a first lumen through which a portion of the inner member passes. The second portion includes a second lumen through which a portion of the inner member passes. In this example, the flexible transmission mechanism is disposed between the first portion and the second portion. The first portion can include a cutting surface disposed distal to the flexible transmission mechanism.

The medical instrument can also include a first cylindrical portion within the inner member and a second cylindrical portion within the outer member. In this example, the first cylindrical portion is disposed concentrically within the second cylindrical portion. The inner member can also include an opening configured to receive a target. The opening can be disposed distal to the curved portion. The cutting surface of the outer member and an edge of the opening can include a sharp edge. The target can include suture and/or biological tissue. The distal end of the inner member can be configured to push a knot. The distal end of the inner member can include a rounded edge. The medical instrument can also include an actuating member coupled to at least one of the inner member and the outer member.

In another aspect, there is a medical instrument including an outer member and an inner member. The outer member has a passage extending therethrough. The inner member is slidably positioned within the passage. The inner member includes a curved portion at its distal region and an opening within the distal region for receiving a target. The inner member and outer member are configured such that when at least one of the inner member and the outer member moves, the target positioned within the opening is cut between an edge of the outer member and an edge of the opening. The medical instrument can include one or more of the following features. The outer member can include a flexible portion at a distal region of the outer member. The edge of the outer member can be disposed distal to the flexible member.

The flexible portion of the outer member can have less material than another portion of the outer member that is less flexible than the flexible portion. The passage can include a wall defining the passage. In this example, the wall does not fully enclose the passage within the flexible portion of the outer member. The wall of the flexible portion of the outer member can be disposed on a concave side of the curved portion of the inner member. The wall within the flexible portion of the outer member encloses approximately a range of 30% to 40% of the circumference of the passage. The outer member can include a first less-flexible portion and a second less-flexible portion. The first less-flexible portion includes the edge of the outer member, and is disposed distal to the flexible member. The second less-flexible portion is disposed proximal to the flexible portion. In this example, the flexible portion is configured to conform to the curved portion while transferring motional forces from the second less-flexible portion to the first less-flexible portion. The motional forces can include linear and/or rotational forces.

The outer member can include a first portion and a second portion. The first portion includes a first lumen through which a portion of the inner member passes. The second portion includes a second lumen through which a portion of the inner member passes. In this example, the flexible portion is disposed between the first portion and the second portion. The first portion can include the edge of the outer member and can be disposed distal to the flexible portion. The medical instrument can include a first cylindrical portion within the inner member and a second cylindrical portion within the outer member. In this example, the first cylindrical portion is disposed concentrically within the second cylindrical portion.

The opening can be disposed on a side of the inner member in contact with the outer member. The opening can be disposed at a distal end of the curved portion. The opening can be disposed distal to the curved portion. The edge of the outer member and/or the edge of the opening can include a sharp edge. The distal end of the inner member can be configured to push a knot. The distal end of the inner member can include a rounded edge. The medical instrument can also include an actuating member coupled to at least one of the inner member and the outer member. The target can include suture and/or biological tissue.

In another aspect, there is a method for generating a curved medical instrument. The method includes bending an inner member to form a curve at a distal region of the inner member and providing an outer member with a passage, where the passage is sized to allow the inner member to pass therethrough. The method also includes removing a portion of a wall of the outer member at a distal region of the outer member. The method can also include providing the inner member with an opening, where the opening sized to receive a target, and where bending further comprises bending the inner member to form a curve proximal to the opening.

The method can also include providing a cutting surface adjacent the opening. The method can also include providing a cutting surface on the outer member adjacent the removed portion of the wall. The method can also include providing a cutting surface at a distal end of the outer member. The method can also include locating the inner member concentrically within the outer member. The method can also include coupling an actuating member to the inner member and/or the outer member. The method can also include rounding an edge of a distal tip of the inner member.

In another aspect, there is a method for using a curved medical instrument. The method includes moving an outer member and/or an inner member concentrically disposed within the outer member, to cause the outer member to slide over an opening disposed distal to a curved portion of the inner member and to cut a target extending through the opening. In an example where the target include a flexible fixating member, such as suture, the method can also include threading the flexible fixating member through the opening of the inner member. The method can also include pushing a knot with a distal end of the inner member. The details of one or more embodiments of the invention are set forth in the accompanying drawings and the description below. Other features, objects, and advantages of the invention will be apparent from the description and drawings, and from the claims.

DESCRIPTION OF DRAWINGS

Like reference symbols in the various drawings indicate like elements.

DETAILED DESCRIPTION

Figure 1A:
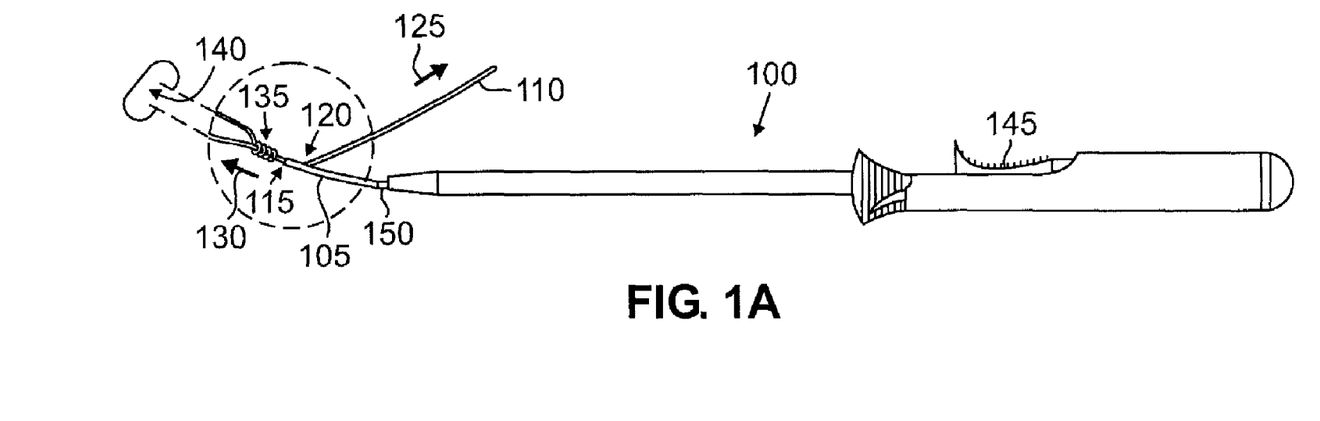
FIG. 1A is a side view of a curved medical instrument.

FIG. 1A illustrates a curved medical instrument 100 that serves both as a suture cutter and a knot pusher. The distal end of instrument 100 has a curved inner member 105, which is positioned within an outer member 150. Curved inner member 105 is cylindrical in shape and has a channel through which a surgeon threads suture 110. The surgeon introduces suture 110 into the channel through an opening at the distal tip 115 and exits at an opening 120, located on the side of inner member 105. In operation, the surgeon pulls suture 110 in the direction of arrow 125 while moving instrument 100 in the direction of arrow 130 until distal tip 115 touches knot 135. The surgeon continues moving instrument 100 in the direction of arrow 130, while pulling suture 110 in the direction of arrow 125. This pushes knot 135 in the direction of arrow 130 towards surgical site 140. This allows the surgeon to tension a pre-tied knot 135 or tie a knot outside of the body and push knot 135 to surgical site 140 within the body to secure the repair.

Figure 1B:
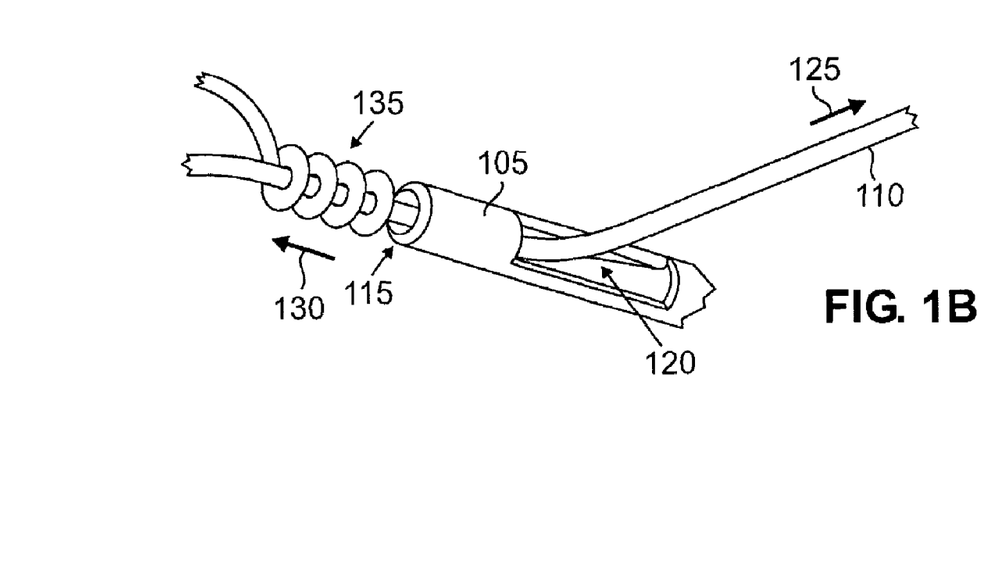
FIG. 1B is a close-up view of the distal end of the curved medical instrument of FIG. 1A.

Once knot 135 is in place to secure the repair, the surgeon uses instrument 100 to cut any excess suture 110. The surgeon slides trigger 145 towards the distal end of instrument 100. Trigger 145 connects to the cylindrical outer member 150 and moves outer member 150 towards the distal end of instrument 100. Outer member 150 is configured, as described below, such that it can conform to the curve of inner member 120 while sliding along and over inner member 120. Outer member 150 slides over curved inner member 105 and eventually reaches opening 120. As outer member 150 slides over opening 120, the distal tip of outer member 150 pinches suture 110 against a distal side of opening 120, cutting suture 110 at opening 120, as will be described in more detail below. FIG. 1B illustrates a close-up view of the distal end of instrument 100.

Figure 2A:
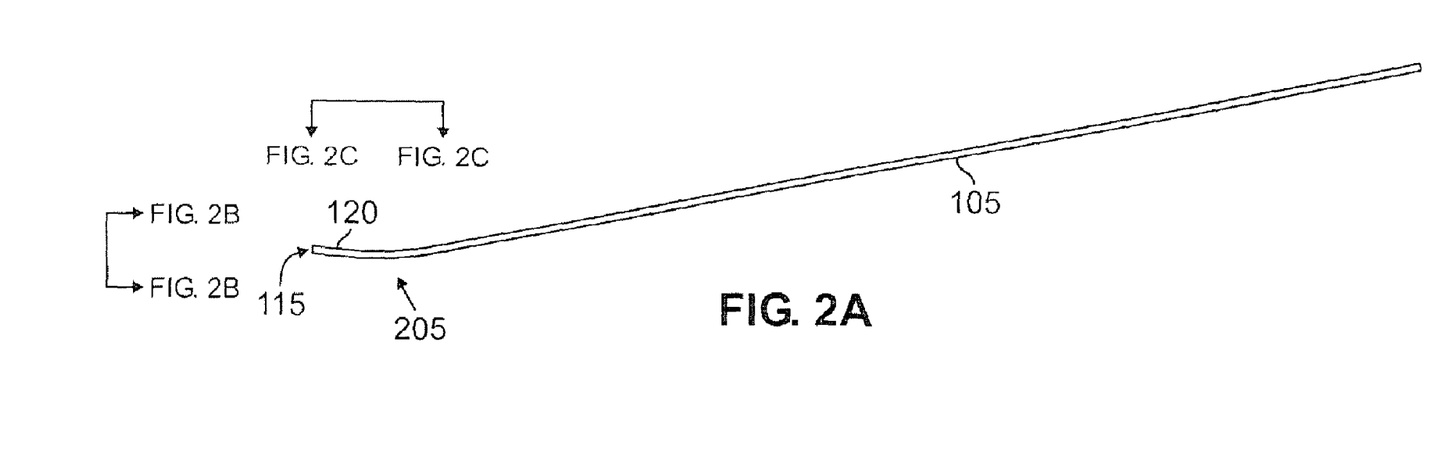
FIG. 2A is a side view of an inner member of the curved medical instrument.
Figure 2B:
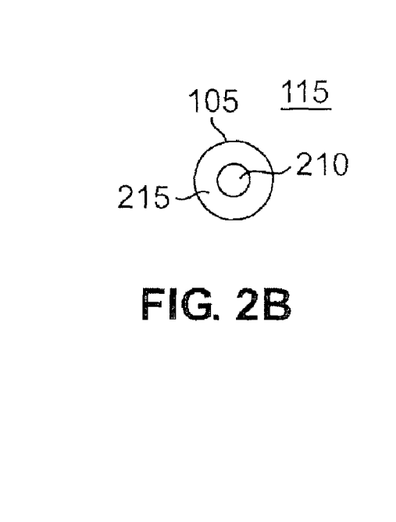
FIG. 2B is a front view of the inner member of FIG. 2A.

As described above, outer member 150 slides along and over curved inner member 105, which includes distal tip 115 for pushing knot 135 and opening 120 through which suture 110 passes. FIGS. 2A-F illustrate the inner member 105 in more detail. FIG. 2A shows inner member 105 removed from medical instrument 100. As shown, inner member 105 includes a curved portion 205 at a distal region. As show in FIG. 2B, distal tip 115 of inner member 105 includes an opening 210 through which the surgeon threads the suture 110. The diameter of opening 210 is sized so that it is not much larger than the diameter of suture 110. This allows suture 110 to pass freely through opening 210, but prevents a knot (e.g., knot 135, FIG. 1) from passing through opening 210. Instead, wall material 215 pushes the knot while the surgeon pulls a single thread of suture 110 through opening 210. There are other possible configurations for distal tip 115, as described in the alternatives below.

Figure 2C:
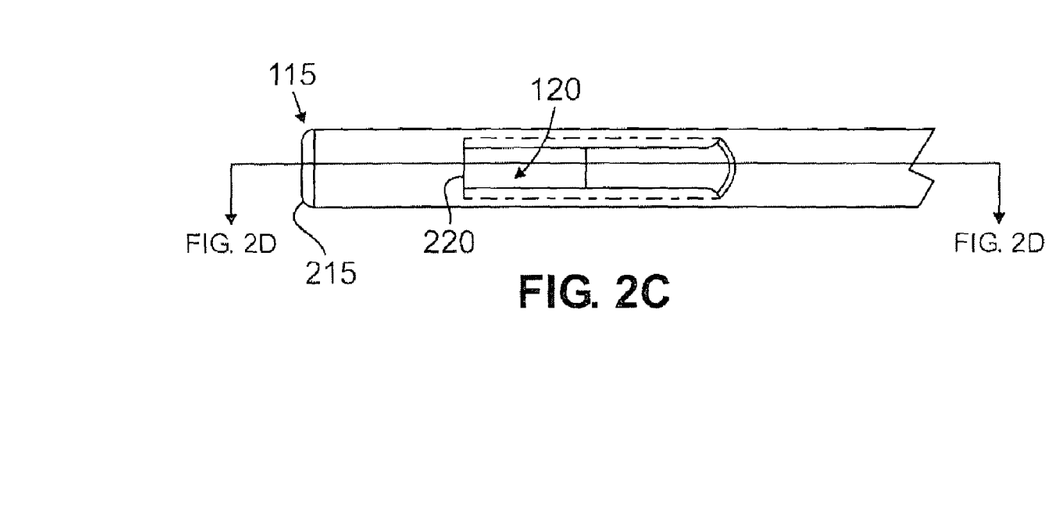
FIG. 2C is a top view of the inner member of FIG. 2A.
Figure 2D:
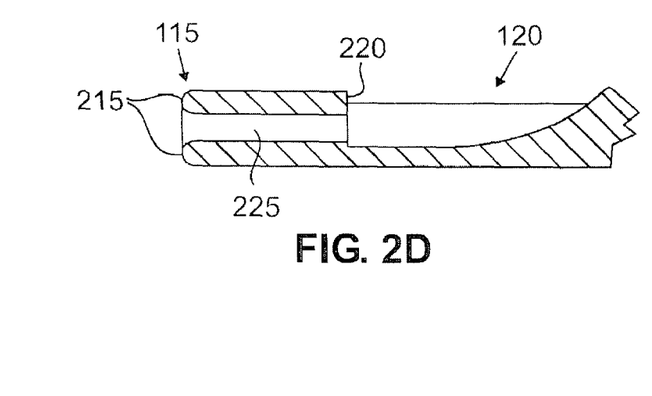
FIG. 2D is a cross-sectional side view of the inner member of FIG. 2C.
Figure 2E:
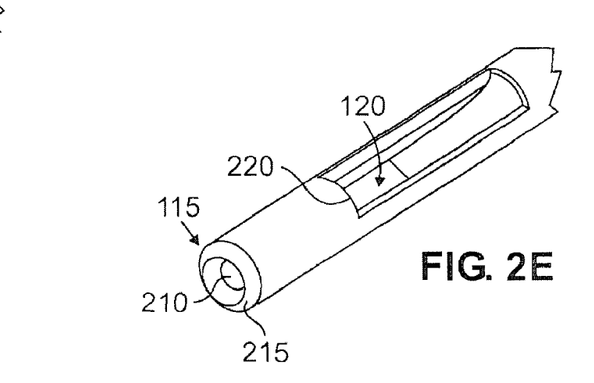
FIG. 2E is a perspective view of the inner member of the curved medical instrument.

As shown in FIG. 2C, the distal end of opening 120 includes a cutting surface 220 against which suture 110 is pushed during the cutting process. Cutting surface 220 can also include a sharp edge to assist in the cutting process. FIGS. 2D and 2E illustrate a channel 225 through which suture 110 passes when the surgeon is pushing a knot as described above. Wall material 215 at distal tip 115 is rounded.

Figure 3A:
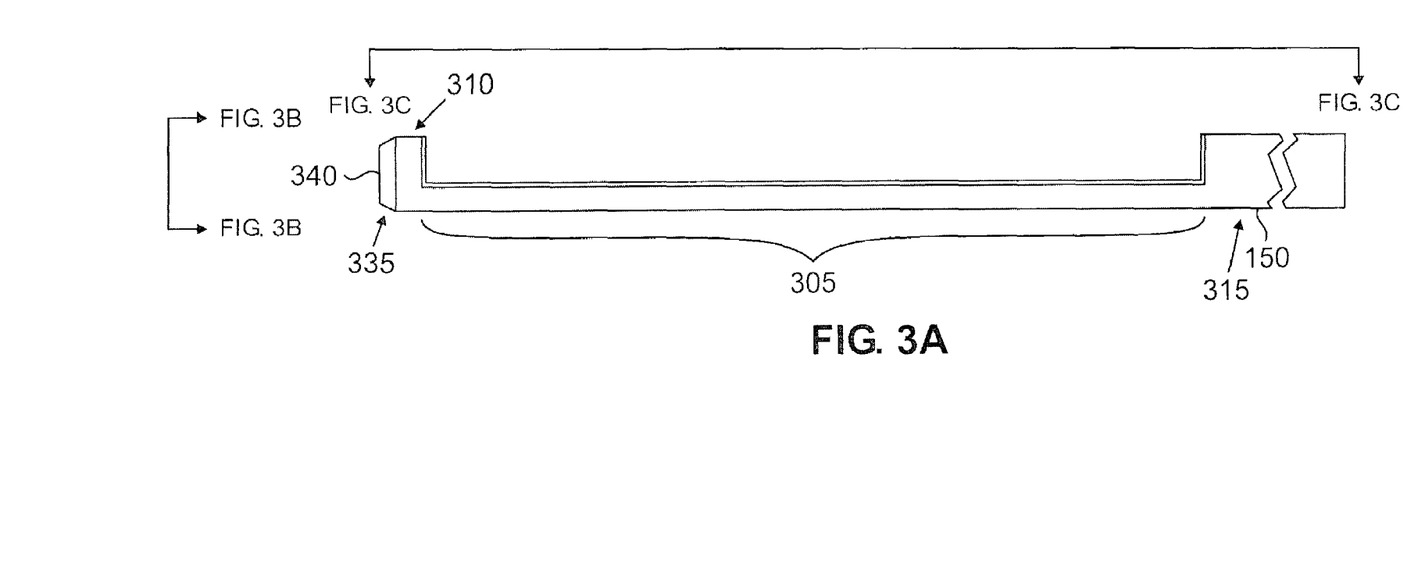
FIG. 3A is a side view of an outer member of the curved medical instrument.
Figure 3B:
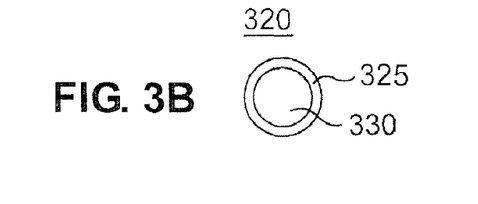
FIG. 3B is a cross-sectional transverse view of portions of the outer member of FIG. 3A.

As described above, outer member 150 slides along and over inner member 105 during the cutting process. FIGS. 3A-D illustrate outer member 150 in more detail. FIG. 3A shows the outer member 150 removed from medical instrument 100. As shown, the distal region of outer member 150 includes a flexible portion 305 that accommodates and conforms to curved region 205 (FIG. 2A) as outer member 150 slides over and along inner member 105. Outer member 150 also includes a less-flexible portion 310 distal to flexible portion 305 and a less-flexible portion 315 proximal to flexible portion 305. For ease of understanding, portions 310 and 315 are referred to as distal portion 310 and proximal portion 315, indicating their positions relative to flexible portion 305. FIG. 3B shows a transverse cross-sectional view 320 of portions 310 and 315. Wall material 325 encloses a circular passage 330, through which inner member 105 passes. The diameter of passage 330 is sized so that it is not much larger than the diameter of inner member 105. This allows portions 310 and 315 to slide freely over and along the cylindrical inner member 105.

Figure 3C:
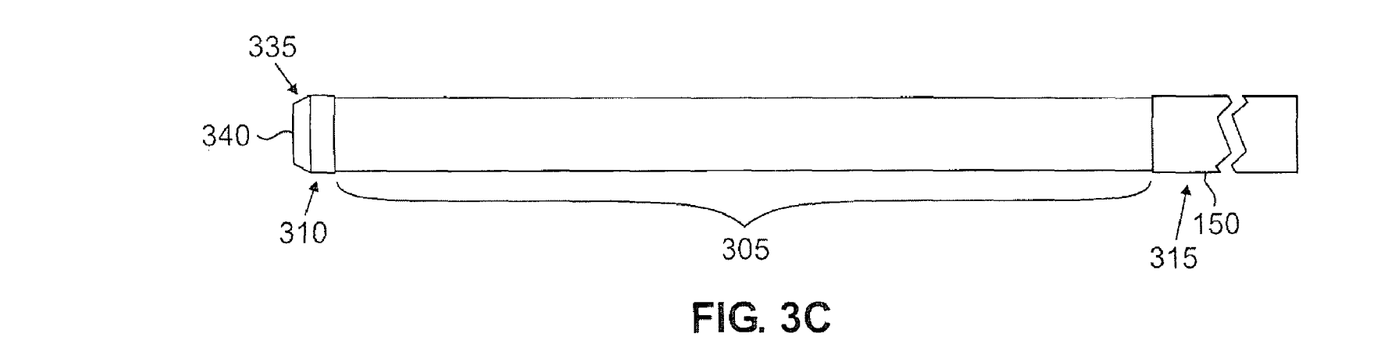
FIG. 3C is a top view of the outer member of FIG. 3A.
Figure 3D:
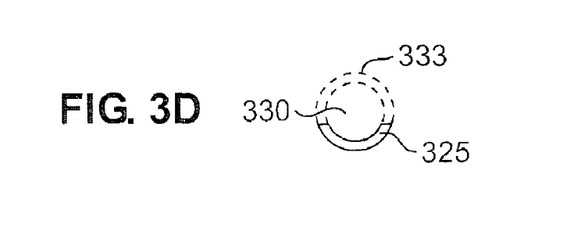
FIG. 3D is a cross-sectional front view of a flexible portion of the outer member.

Flexible region 305 accommodates both being flexible enough to conform to curved portion 205 and being strong enough to push distal portion 310 as a surgeon moves trigger 145 (FIG. 1), connected to proximal portion 315 of outer member 150. As shown in FIGS. 3A and 3C, this is accomplished by removing some of the wall material 325 enclosing passage 330 along flexible portion 305. In the illustrated example of FIG. 3D, wall material 325 is removed from about a range of 60% to 70% of the circumference (indicated by dashed line 333) of passage 330 along flexible portion 305.

Referring back to FIGS. 3A and 3C, proximal portion 315 does not extend over the curve of curved portion 205 (FIG. 2) of inner member 105. Thus, proximal portion 315 does not have to be flexible enough to accommodate and conform to curved portion 205. Distal portion 310, however, does extend along and over curved portion 205 of inner member 105. As described below, distal tip 335 of outer member 150 cuts suture 110. To accommodate both being able to travel along curved portion 205 and being sufficiently rigid to be able to cut suture 110, the length of distal portion 310 is relatively small compared to the radius of curved portion 205. The length of flexible portion 305 is large enough to allow distal portion 310 to accomplish cutting while preventing proximal portion 315 from reaching the curve of curved portion 206. The distal tip 335 of distal portion 310 includes a cutting surface 340 that pushes against suture 110 during the cutting process. Cutting surface 340 can also include a sharp edge to assist in the cutting process.

Figure 4A:
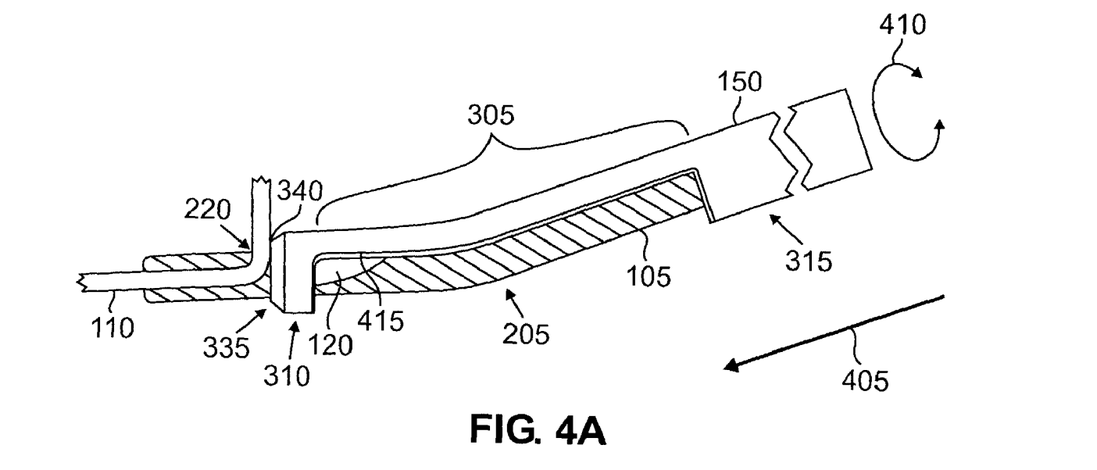
FIG. 4A is a side view of the inner member and the outer member during a cutting process.

FIG. 4A illustrates inner member 105 and outer member 150 during the cutting process. To better show suture 110 in channel 225 (FIG. 2D), FIG. 4A represents inner member 105 using a side cross-sectional view (i.e., an extended view of FIG. 2D). During the cutting process, a surgeon moves trigger 145 (FIG. 1) towards the distal end of outer member 150. Trigger 145 is connected to the proximal portion 315 and causes outer member 150 to move towards the distal end, as indicated by arrow 405. Distal portion 310 of outer member 150, being relatively short, moves along and over curved region 205 without having to adapt its form. Flexible portion 305, however, does bend to adapt and conform to curved portion 205. As outer member 150 moves along in the direction indicated by arrow 405, the distal tip 335 of outer member 150 eventually encounters suture 110 that is extending beyond opening 120 of inner member 105. As distal tip 335 encounters suture 110, suture 110 becomes pinched between cutting surface 220 of inner member 105 and cutting surface 340 of outer member 150. As outer member 150 continues to move distally, the cutting surfaces 220 and 340 compress and eventually cut through suture 110. As described above, sharp edges can be included on either or both cutting surfaces 220 and 340 to assist in this cutting process.

Figure 4B:
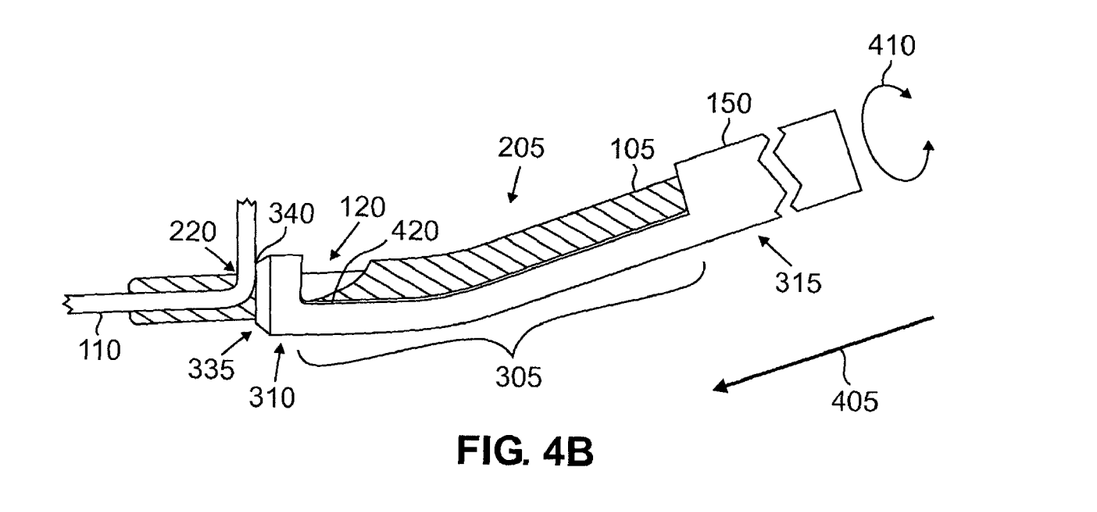
FIG. 4B is a side view of another example of the inner member and the outer member during a cutting process.

As shown in FIG. 4A, the wall 325 of flexible portion 305 is disposed on the concave side of curved portion 205. FIG. 4B shows an example in which flexible portion 305 is disposed on the convex side of curved portion 205. In some of the examples described above, for clarity, the motion of outer member 150 is described as linear along the concentric axis. In other words, the position of outer member 150 is fixed with respect to rotation about the concentric axis. The motion of outer member 150, however, is not limited to only linear motion. As shown in FIGS. 4A and 4B, outer member 150 can also rotate about the concentric axis in either direction, as indicated by arrows 410. As described above, the flexible portion 305 is a flexible transmission mechanism that can translate both linear and rotational forces from an actuating mechanism.

With rotational transmission as an alternative or in addition to the linear transmission, flexible portion 305 enables a surgeon to use medical instrument 100 for additional procedures beyond the linear cutting described above. For example, a surface 415, 420, and/or a portion thereof of the wall of flexible portion 305 can be a cutting surface during rotational motion in the directions of arrows 410. Surfaces 415, 420, and/or a portion thereof can also include sharp edges. Suture 110 can be located on the proximal side of distal portion 310. As outer member 150 is rotated, surface 410 or 415 pinches and cuts any portion of suture 110 extending beyond opening 120. In addition to cutting suture, a surgeon can use medical device 100 to cut tissue. For example, a surgeon can place opening 120 over a polyp and using rotational and/or linear motion, cut to polyp similar to any of the cutting procedures described above, and remove the polyp from the surgical site. To perform complex procedures, medical instrument 100 can include two or more outer members. Similar to outer member 150, the additional outer member (not shown) includes a passage, through which inner member 105 and outer member 150 passes, and a flexible member that accommodates and conforms to curved region 205 (FIG. 2A) as the alternative outer member (not shown) slides over and along inner member 105 and outer member 150. Outer member 150 and the alternative outer member (not shown) can be actuated independently from one another.

To provide another example, the dimensions and materials for an example medical instrument 100' (not shown) follow. Curved portion 205 is located within 1.00 inch from distal tip 115. The inside radius of the curve of curved portion 205 is 2.25 inches, with a tolerance of 0.25 inches. Opening 120 is located within 0.41 inches from distal tip 115. The diameter of channel 225 is 0.024 inches. The diameter of passage 330 of outer member 150 is 0.065 inches. The diameter of outer member 150 is 0.083 inches. The length of distal region 310 is 0.05 inches. The length of flexible portion 305 is 0.95 inches. The inner member 105 is made out of 17-4 PH stainless steel. The outer member 150 is made out of 304 stainless steel.

A number of embodiments of the invention have been described. Nevertheless, it will be understood that various modifications may be made without departing from the spirit and scope of the invention. For example only and not to limit other alternatives, the distal tip and channel of the inner member can have different configurations. The diameter of the distal tip and channel can be sized to accommodate two strands of suture, so that the surgeon can pull the suture for both ends of a knot, for example a square knot. Also, although the term suture is used for clarity, the invention is not limited to use with only suture. Any flexible fixating material to effect a repair can be used. Also, the elements of the medical instrument that move can vary. For example, the trigger can move the inner member while the outer member remains stationary. The trigger can also move both the inner member and the outer member simultaneously in opposite directions. Similarly, if more than one outer member is used, the inner member and/or any combination of outer members can be configured to move with one or more actuating mechanisms. Also, although the inner and outer members are described using circular and cylindrical geometries, the invention can also be used with other geometries, such a squares, polygons and the like. Accordingly, other embodiments are within the scope of the following claims.

What is claimed is:

1. A medical instrument comprising:
   an inner member having a rigid, curved portion at a distal region of the inner member and having a cutting surface, the rigid, curved portion being formed with at least a fixed concave side along a longitudinal axis of the inner member; and
   an outer member concentrically and movably coupled to the inner member, the outer member including a cutting surface and the outer member being more flexible than the rigid, curved portion of the inner member such that when the outer member slides over the rigid, curved portion, the outer member is caused to bend along the longitudinal axis to conform to the rigid, curved portion,
   wherein the inner member and outer member are configured such that a longitudinal sliding movement of the outer member over the inner member acts to cut a target through contact with the cutting surface of the inner member and the cutting surface of the outer member.

2. The medical instrument of claim 1, wherein the outer member includes a flexible transmission mechanism at a distal region of the outer member.

3. The medical instrument of claim 2 wherein the flexible transmission mechanism of the outer member comprises less material than another portion of the outer member that is less flexible than the flexible transmission mechanism.

4. The medical instrument of claim 2 wherein the outer member further comprises:
   a wall defining a passage through which the inner member passes, and
   wherein the wall does not fully enclose the passage within the flexible transmission mechanism of the outer member.

5. The medical instrument of claim 4 wherein the wall of the flexible transmission mechanism of the outer member is disposed on a concave side of the curved portion of the inner member.

6. The medical instrument of claim 4 wherein the wall within the flexible transmission mechanism of the outer member encloses approximately a range of 30% to 40% of the circumference of the passage.

7. The medical instrument of claim 2 wherein the outer member further comprises:
   a first less-flexible portion disposed distal to the flexible transmission mechanism; and
   a second less-flexible portion disposed proximal to the flexible transmission mechanism,
   wherein the flexible transmission mechanism is configured to conform to the curved portion while transferring motional forces from the second less-flexible portion to the first less-flexible portion.

8. The medical instrument of claim 7 wherein the motional forces comprise at least one of linear and rotational forces.

9. The medical instrument of claim 2 wherein the outer member further comprises:
   a first portion including a first lumen through which a portion of the inner member passes; and
   a second portion including a second lumen through which a portion of the inner member passes,
   wherein the flexible transmission mechanism is disposed between the first portion and the second portion.

10. The medical instrument of claim 9 wherein the first portion includes the cutting surface disposed distal to the flexible transmission mechanism.

11. The medical instrument of claim 1 further comprising:
    a first cylindrical portion within the inner member; and
    a second cylindrical portion within the outer member,
    wherein the first cylindrical portion is disposed concentrically within the second cylindrical portion.

12. The medical instrument of claim 1 wherein the inner member further comprises an opening configured to receive a target.

13. The medical instrument of claim 12 wherein the opening is disposed distal to the curved portion.

14. The medical instrument of claim 12 wherein an edge of the opening comprises the cutting surface of the inner member.

15. The medical instrument of claim 12 wherein the target comprises suture.

16. The medical instrument of claim 12 wherein the target comprises biological tissue.

17. The medical instrument of claim 12 wherein the opening is defined by a sidewall of the inner member, the sidewall extending from the distal region of the inner member to a proximal region of the inner member.

18. The medical instrument of claim 17, wherein the sidewall is a circumferential sidewall.

19. The medical instrument of claim 12 wherein the opening is offset from a longitudinal axis of the inner member.

20. The medical instrument of claim 12 wherein the opening is proximal to a distal end surface of the inner member.

21. The medical instrument of claim 1 wherein a distal end of the inner member is configured to push a knot.

22. The medical instrument of claim 1 wherein a distal end of the inner member comprises a rounded edge.

23. The medical instrument of claim 1 further comprising an actuating member coupled to at least one of the inner member and the outer member.

24. The medical instrument of claim 1, wherein:
    the outer member has a passage extending therethrough;
    the inner member is slidably positioned within the passage;
    the inner member includes an opening within the distal region;

the inner member and outer member are configured such that the longitudinal sliding movement of the outer member over the inner member positioned within the passage acts to cut a target positioned within the opening;

the cutting surface of the outer member comprises an edge of the outer member; and the cutting surface of the inner member comprises an edge of the opening.

25. The medical instrument of claim 24 wherein the outer member further comprises a flexible portion at a distal region of the outer member.

26. The medical instrument of claim 25 wherein the edge of the outer member is disposed distal to the flexible member.

27. The medical instrument of claim 25 wherein the flexible portion of the outer member comprises less material than another portion of the outer member that is less flexible than the flexible portion.

28. The medical instrument of claim 25 wherein the passage further comprises:

a wall defining the passage, and wherein the wall does not fully enclose the passage within the flexible portion of the outer member.

29. The medical instrument of claim 28 wherein the wall of the flexible portion of the outer member is disposed on a concave side of the curved portion of the inner member.

30. The medical instrument of claim 28 wherein the wall within the flexible portion of the outer member encloses approximately a range of 30% to 40% of the circumference of the passage.

31. The medical instrument of claim 25 wherein the outer member further comprises:

a first less-flexible portion including the edge of the outer member, the first less-flexible portion disposed distal to the flexible member; and a second less-flexible portion disposed proximal to the flexible portion, wherein the flexible portion is configured to conform to the curved portion while transferring motional forces from the second less-flexible portion to the first less-flexible portion.

32. The medical instrument of claim 25 wherein the outer member further comprises:

a first portion including a first lumen through which a portion of the inner member passes; and a second portion including a second lumen through which a portion of the inner member passes, wherein the flexible portion is disposed between the first portion and the second portion.

33. The medical instrument of claim 32 wherein the first portion includes the edge of the outer member and is disposed distal to the flexible portion.

34. The medical instrument of claim 25 further comprising:

a first cylindrical portion within the inner member; and a second cylindrical portion within the outer member, wherein the first cylindrical portion is disposed concentrically within the second cylindrical portion.

35. The medical instrument of claim 24 wherein the opening is disposed on a side of the inner member in contact with the outer member.

36. The medical instrument of claim 24 wherein the opening is disposed at a distal end of the curved portion.

37. The medical instrument of claim 24 wherein the opening is disposed distal to the curved portion.

38. The medical instrument of claim 24 wherein at least one of the edge of the outer member and the edge of the opening comprises a sharp edge.

39. The medical instrument of claim 24 wherein a distal end of the inner member is configured to push a knot.

40. The medical instrument of claim 24 wherein a distal end of the inner member comprises a rounded edge.

41. The medical instrument of claim 24 further comprising an actuating member coupled to at least one of the inner member and the outer member.

42. The medical instrument of claim 24 wherein the target comprises suture.

43. The medical instrument of claim 24 wherein the target comprises biological tissue.

44. The medical instrument of claim 24 wherein the edge of the opening comprises a cutting surface.

45. The medical instrument of claim 44 wherein the opening cutting surface includes a sharp edge.

46. The medical instrument of claim 24 wherein the opening is defined by a sidewall of the inner member.

47. The medical instrument of claim 46, wherein the sidewall is a circumferential sidewall.

48. The medical instrument of claim 24 wherein the inner member includes a distal end surface that defines a second opening, the second opening being different than the opening within the distal region.

49. The medical instrument of claim 24 wherein the outer member comprises a tube and the inner member includes a lumen.

50. The medical instrument of claim 24 wherein the opening is offset from a longitudinal axis of the inner member.

51. The medical instrument of claim 24 wherein the opening is proximal to a distal end surface of the inner member.

52. The medical instrument of claim 1 wherein the outer member cutting surface includes a sharp edge.

53. The medical instrument of claim 1 wherein the inner member cutting surface includes a sharp edge.

54. The medical instrument of claim 1 wherein the inner member includes a distal end surface that defines an opening, the inner member being coupled to the outer member to allow relative longitudinal movement between the inner member and the outer member.

55. The medical instrument of claim 1 wherein the outer member comprises a tube, the inner member includes a lumen, and the outer member and the inner member are coupled together to allow relative movement between the inner member and the outer member.

56. The medical instrument of claim 1, wherein the cutting surface of the outer member is at a distal end surface of the outer member.

57. A medical instrument comprising:

an inner member having a curved portion at a distal region of the inner member and having a cutting surface; and an outer member concentrically and movably coupled to the inner member, the outer member having a distal end surface including a cutting surface and the outer member including a flexible transmission mechanism at a distal region of the outer member, wherein at least one of the inner member and the outer member is configured to longitudinally slide relative to the other of the inner member and the outer member such that the cutting surface of the inner member and the cutting surface of the outer member together act to cut a target, wherein the outer member further comprises a wall defining a passage through which the inner member passes, wherein the wall does not fully enclose the passage within the flexible transmission mechanism of the outer member, and wherein the wall within the flexible transmission mechanism of the outer member encloses approximately a range of 30% to 40% of the circumference of the passage.

58. A medical instrument comprising:

an outer member having a passage extending therethrough; and an inner member slidably positioned within the passage, the inner member including a curved portion at a distal region of the inner member, the curved portion being rigid such that when the outer member slides over the curved portion, the outer member is caused to bend along the curved portion, and an opening within the distal region, wherein the inner member and outer member are configured such that a longitudinal sliding movement of the inner member within the passage acts to cut a target positioned within the opening through contact with an edge of the outer member and an edge of the opening, wherein the passage further comprises a wall defining the passage, wherein the wall does not fully enclose the passage within the flexible portion of the outer member, and wherein the wall within the flexible portion of the outer member encloses approximately a range of 30% to 40% of the circumference of the passage.

\* \* \* \* \*